US00PP17453P2

(12) United States Plant Patent
Frazer

(10) Patent No.: US PP17,453 P2
(45) Date of Patent: Feb. 27, 2007

(54) ***DIEFFENBACHIA* PLANT NAMED 'MARY'**

(50) Latin Name: *Dieffenbachia hybrida*
Varietal Denomination: Mary

(76) Inventor: Edwin John Frazer, P.O. Box 200, Kenmore, Queensland, 4069 (AU)

( * ) Notice: Subject to any disclaimer, the term of this patent is extended or adjusted under 35 U.S.C. 154(b) by 0 days.

(21) Appl. No.: 11/237,506

(22) Filed: Sep. 28, 2005

(51) Int. Cl.
*A01H 5/00* (2006.01)

(52) U.S. Cl. ..... Plt./378
(58) Field of Classification Search ..... Plt./378
See application file for complete search history.

*Primary Examiner*—Kent Bell
*Assistant Examiner*—Annette H Para

(74) *Attorney, Agent, or Firm*—Paul S. Rooy P.A.

(57) ABSTRACT

'Mary', a *Dieffenbachia* cultivar. 'Mary' is a compact *Dieffenbachia* of medium size, with oval, yellow-green variegated leaves emarginated in dark green. The leaves are held tightly to the stem with distinctive short white petioles. 'Mary' exhibits strong suckering ability. Its plant growth habit is small and compact, leaf shape is oval, leaf size is approximately 23 cm×14 cm with a length to width ratio of 1.6, leaves are yellow green and variegated, petioles are predominately white, and the distance from apex of wing to leaf base is small and bout 0.5 cm.

2 Drawing Sheets

Latin name of the genus and species of the plant claimed: The plant genus is *Dieffenbachia*. The plant species is *hybrida*.

FIELD OF THE INVENTION

The present invention comprises a new and distinct cultivar of *Dieffenbachia* which is named 'Mary'. Its genus is *Dieffenbachia*. The plant species is *hybrida*. Its market class is that of ornamental potted plants. 'Mary' is a perennial plant, and is intended for use in landscaping, and as a decorative potted plant.

DESCRIPTION OF PRIOR ART

'Mary' is the product of a planned breeding program carried out in 2001 and 2002 at Brookfield, Queensland, Australia. Pollination occurred in October 2001 and the selection was made in late 2002. Mary's Ely's seed parent was *Dieffenbachia* 'Tiki', and its pollen parent was an unnamed seedling from a breeding program conducted by the breeder.

Uniformity:

*Dieffenbachia* 'Mary' was first asexually reproduced in January 2004 by tissue culture. The plant is a perennial. The plant is stable as evidenced by the uniformity and stability of propagation via tissue culture since then. Propagation was carried out at Leumeah, NSW Australia.

No off-types have been observed throughout the trial period. The variety is considered to be uniform and stable in all characteristics.

SUMMARY OF THE INVENTION

The major characteristics of 'Mary' include a plant growth habit that is small and compact, leaf shape is oval, leaf size is approximately 23 cm×14 cm with a length to width ratio of 1.6, leaves are yellow green and variegated, petioles are predominately white, and the distance from apex of wing to leaf base is small and about 0.5 cm.

The following traits have been repeatedly observed and are determined to be basic characteristics of the new *Dieffenbachia* variety 'Mary', which in combination distinguish 'Mary' from other *Dieffenbachia* of the same general type, for example the well-known cultivar 'Perfection' (unpatented), the parental variety 'Tiki' (U.S. Plant Pat. No. 7,298), and 'Ely', subject of co-pending U.S. Plant patent application Ser. No. 11/237,504 for *Dieffenbachia hybrida* plant named 'Ely'. The measurements refer to saleable size plants in 140 mm pots grown as an indoor plant.

1) The 'Mary' plant growth habit is compact (height 35 cm, width 45 cm), while 'Perfection' is taller and compact (height 40 cm, width 45 cm), and 'Tiki' is not so compact (height 45 cm, width 40 cm), while 'Ely' is compact (height 30 cm, width 45 cm).
2) The leaf shape of 'Mary' is oval, 'Perfection' is ovate to oval, 'Tiki' is oblong to oval, and 'Ely' is orbicular to oval.
3) The 'Mary' leaf apex shape is rounded with small point, 'Perfection' is acute, 'Tiki' is acute, and 'Ely' is rounded with small point.
4) The 'Mary' leaf size is approximately 23 cm×14 cm and its length to width ratio is 1.6, 'Perfection' leaf size measures 23 cm×10 cm and its length to width ratio 2.3, 'Tiki' leaf size measures 27 cm×10 cm and its length to width ratio is 2.7, and 'Ely' leaf size is 25 cm×17 cm and its length to width ratio is 1.5. Note that a smaller length to width ratio indicates a wider leaf.
5) The 'Mary' leaf petiole predominant color is white, 'Perfection' is light green, 'Tiki' is light green, and 'Ely' is white.
6) The 'Mary' leaf positioning is about horizontal, 'Perfection' is mainly upright, 'Tiki' is mainly upright, and 'Ely' is about horizontal.
7) The 'Mary' distance from apex of wing to leaf base is about 1 cm, 'Perfection' is about 4 cm, 'Tiki' is about 1 cm, and 'Ely' is about 3 cm.

BRIEF DESCRIPTION OF THE DRAWINGS

The invention, together with the other objects, features, aspects and advantages thereof will be more clearly understood from the following in conjunction with the accompanying drawings.

Two sheets of drawings are provided. Sheet one contains FIG. 1. Sheet two contains FIG. 2.

BOTANICAL DESCRIPTION OF THE PLANT

Figure 1:
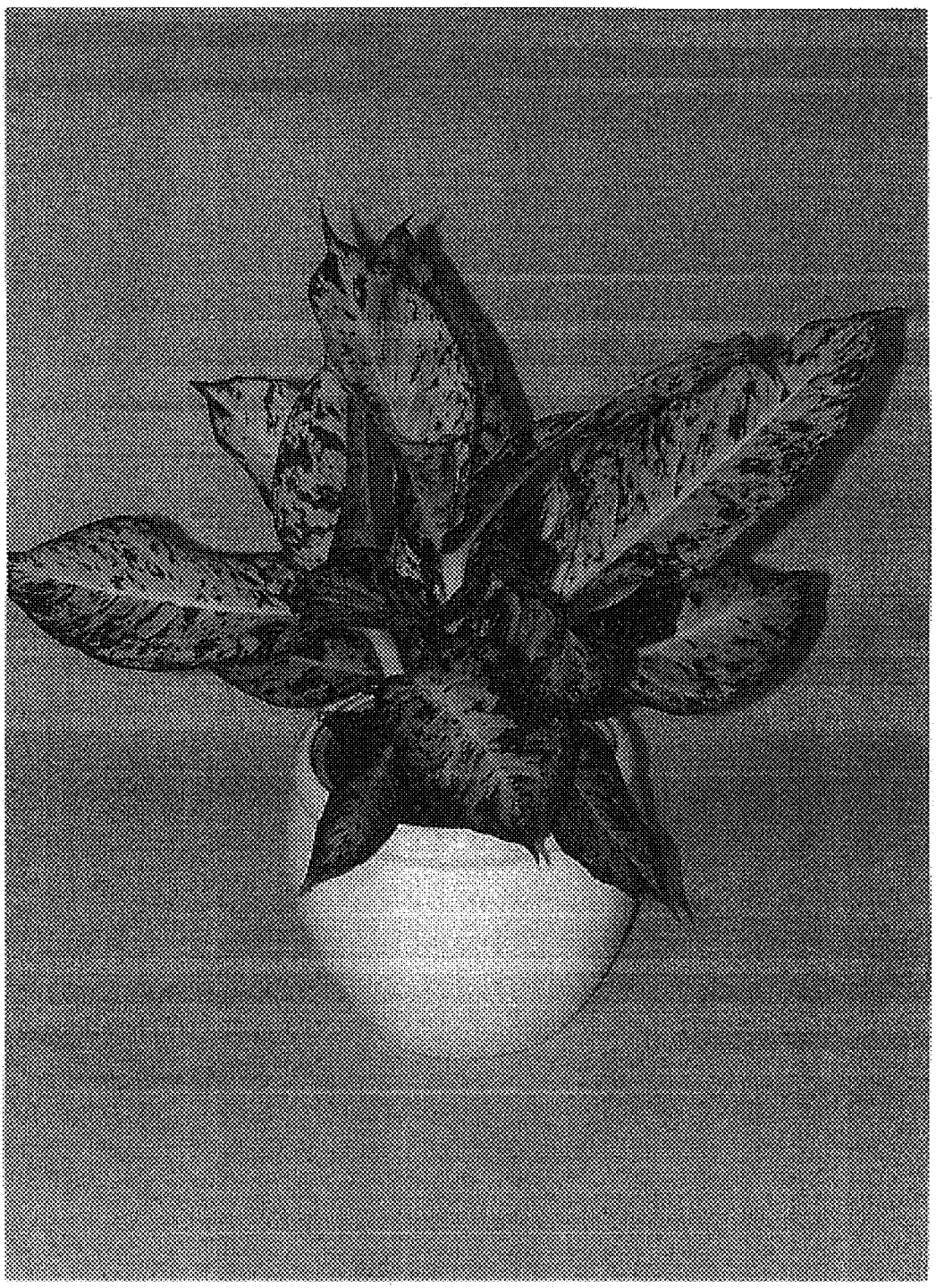
FIG. 1 is a color photograph of an 'Mary' plant in a 140 mm pot grown from a 14 week old liner for 18 weeks under greenhouse growing conditions. This 'Mary' was about 30 cm high measured from soil surface to the tip, and was about 45 cm wide.
Figure 2:
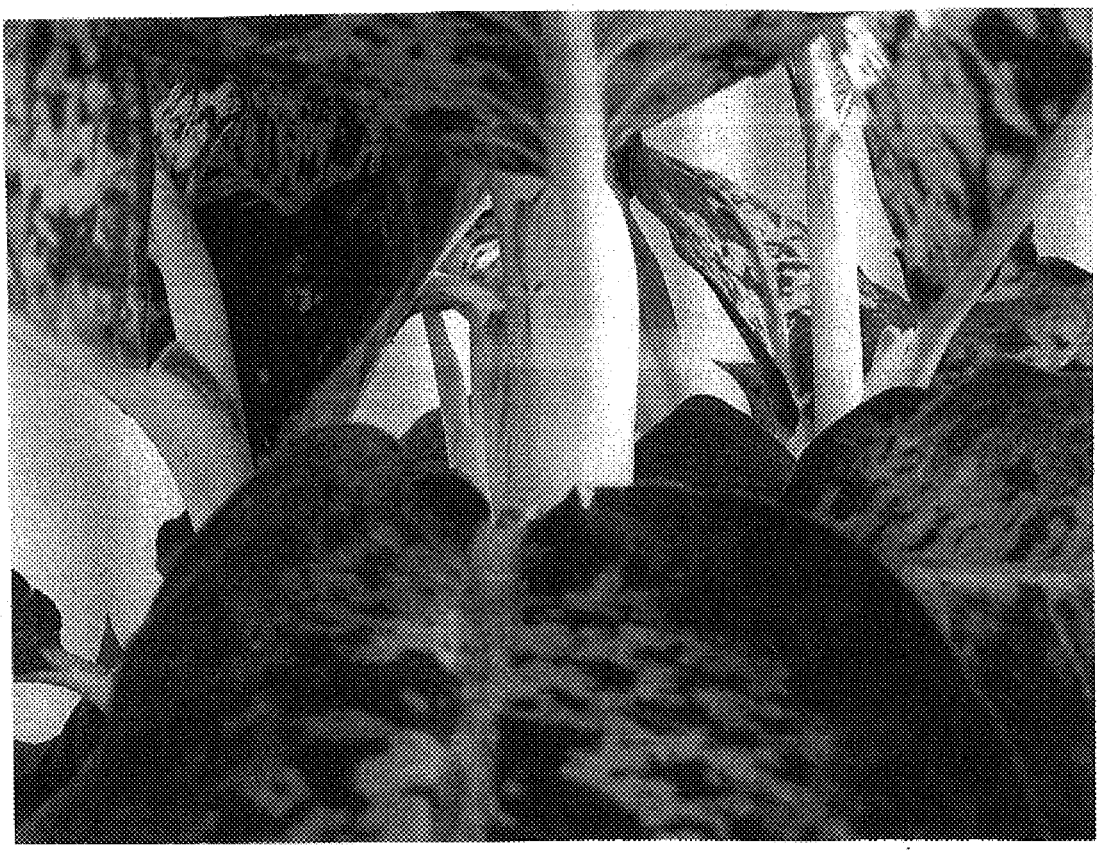
FIG. 2 is a color photograph showing the distinctive white petiole of 'Mary'.

The following Botanical Description describes *Dieffenbachia* 'Mary' plants grown at Wellington Point, Queensland, Australia grown under greenhouse growing conditions. The plant has not been observed under all possible environmental conditions. The phenotype may vary somewhat with variations in environment such as temperature, light intensity and/or fertilizer rate, without, however, any variance in genotype.

Plant: In a 140 mm pot for a plant grown from a 14 week old liner grown for 18 weeks under greenhouse growing conditions, 'Mary' was about 30 cm high measured from soil surface to the tip, and was about 45 cm wide.

Stem:

*Growth pattern.*—The mature stem is approximately 1.8 cm to 2.2 cm in diameter about 5 cm above the soil level. Inter-node distance is approximately 2.0 cm at soil level in mature stem.

*Color.*—Immature stem emerges light green about RHS 137D but fades to whitish about RHS 155B at maturity.

Petiole: The following information is based on the $2^{nd}$ expanded leaf from the apex.

*Growth pattern.*—The petiole has fleshy edges (wings) extending from midrib. The wings are approximately 8.5 cm long, while the whole petiole is about 9 cm long. The apex of the wing is emarginated, and about 10 mm wide at tip.

*Dimensions.*—The petiole is about 9 cm long on average but ranges 7.5 to 10.5 cm. Wing length is about 8.5 cm on average and ranges from about 7.5 to 9.5 cm. The distance between leaf base to tip of apex is small, about 0.5 cm.

*Color.*—The petiole is predominately white RHS155A. The petiole wings (abaxial) are green about RHS 137C which gradually fades out onto mid rib becoming much lighter green, about an RHS 138C.

Leaf:

*Growth pattern.*—The leaf shape is oval, with slight cordate base and acute tip. The leaf is asymmetric with the side of the leaf unrolling first having less surface area then the side unrolling last. The leaf is oriented about 30 degrees to the stem axis at the time of full unrolling, changing to about horizontal to stem and hence exposing the full color of the leaves. The mid rib is straight over the length of leaves, with only some of the lower leaves drooping.

*Dimensions.*—The leaf is approximately 23 cm×14 cm with a length to width ratio of 1.6.

*Midrib.*—Prominent and attractive.

*Primary veins.*—The primary veins are sunken into the upper surface and protrude out of the underside.

*Color and pattern.*—The adaxial surface of new leaves has a midrib color of white RHS 155A and with maturity green specs creep in to the white sections. The leaf edges are dark green about RHS 139A but blend into yellow green about RHS 154D around midribs and main veins. Green specs and spots are present in the leaf blade. The abaxial surface is lighter than the adaxial surface, the edges are about RHS 139C, and the middle is about RHS 154D, similar to the adaxial but only lighter.

*Axillary breaks.*—'Mary' exhibits strong suckering ability, filling the pot quickly and giving a compact appearance.

Inflorescence: The inflorescence consists of an outer spathe which supports the spadix on which central axis several male and female flowers are clustered without any petals. The flower color of 'Mary' includes a peduncle which is almost white, RHS 155A. The spathe is green, about RHS 139C and yellow green RHS 154D. The intensity of the color expression is somewhat dependent on the amount of the exposure of the spathe.

Roots: The roots are thick and white, with fine laterals.

All color codes refer to "The Royal Horticultural Society London, 1995 Ed." Colors and leaf size may vary somewhat depending on horticultural practices such as light levels and fertilizer rates, among other things, without however, any variance in genotype.

I claim:

1. A new and distinct cultivar of *Dieffenbachia* plant named 'Mary', as herein described and illustrated.

* * * * *

UNITED STATES PATENT AND TRADEMARK OFFICE

CERTIFICATE OF CORRECTION

PATENT NO. : PP 17,453 P2
APPLICATION NO. : 11/237506
DATED : February 27, 2007
INVENTOR(S) : Edwin John Frazer It is certified that error appears in the above-identified patent and that said Letters Patent is hereby corrected as shown below:

On Title Page
Item 57
Abstract, last line: Is: "...and bout..." Should be: --...and about...--
Col 1 line 18: Is: "Mary's Ely's seed parent..." Should be: --Mary's seed parent...--

Signed and Sealed this

Seventh Day of August, 2007

JON W. DUDAS
*Director of the United States Patent and Trademark Office*